United States Patent [19]

Isaac et al.

[11] Patent Number: 4,786,498
[45] Date of Patent: Nov. 22, 1988

[54] PROCESS FOR THE PRODUCTION OF CAMOMILE EXTRACTS RICH IN FLAVONES

[75] Inventors: Otto Isaac, Hanau; Reinhold Carle, Rödermark; Bernd Dölle, Langen, all of Fed. Rep. of Germany

[73] Assignee: Degussa Aktiengesellschaft, Frankfurt am Main, Fed. Rep. of Germany

[21] Appl. No.: 153,481

[22] Filed: Feb. 2, 1988

Related U.S. Application Data

[63] Continuation of Ser. No. 862,178, May 12, 1986, abandoned, which is a continuation of Ser. No. 709,085, Mar. 7, 1985, abandoned.

[30] Foreign Application Priority Data

Mar. 16, 1984 [DE] Fed. Rep. of Germany ....... 3409619

[51] Int. Cl.$^4$ .............................................. A61K 35/78
[52] U.S. Cl. .................................. 424/195.1; 426/655; 426/651; 426/388; 426/429
[58] Field of Search ............... 426/651, 388, 429, 655; 424/195.1

[56] References Cited

U.S. PATENT DOCUMENTS 4,584,198  4/1986  Tubaro et al. .................... 424/195.1
4,592,911  6/1986  Behr et al. ........................ 424/195.1

FOREIGN PATENT DOCUMENTS 2331854   1/1975  Fed. Rep. of Germany .
3446216  12/1984  Fed. Rep. of Germany .
3423307   1/1985  Fed. Rep. of Germany .
1560371   2/1980  United Kingdom .
2167955A  6/1986  United Kingdom ................ 426/655

OTHER PUBLICATIONS

Furia et al, Fenaroli's Handbook of Flavor Ingredients, 2nd Ed., 1975, vol. I, CRC Press: Cleveland, Ohio, pp. 298–300.
Merory, Food Flavorings, 1968, 2nd Ed., Avi: Westport, Conn., pp. 92–93.
Lust, The Herb Book, 1974, Benedict Lust Publications, New York, pp. 140–141.
Deutsche Apothecker Zeitung, 97th year, Feb. 1957, pp. 149–151.
European Pharmacopoeia III-1975, pp. 269–271.
Hanke, "Qualitat pflanz. Arzneimittel Wiss. Verlagsges. mbH, Stuttgent, 1984, pp. 98–99.

*Primary Examiner*—Joseph Golian
*Attorney, Agent, or Firm*—Cushman, Darby & Cushman

[57] ABSTRACT

This invention relates to the production of camomile extracts rich in flavone by extracting ordinary camomile drug together with added camomile wing petals.

4 Claims, No Drawings

PROCESS FOR THE PRODUCTION OF CAMOMILE EXTRACTS RICH IN FLAVONES

This is a continuation of application Ser. No. 862,178, filed May 12, 1986, which was abandoned upon the filing hereof, which is a continuation of application Ser. No. 709,085, filed 3/7/85, now abandoned.

BACKGROUND OF THE INVENTION

A whole drug is normally used for the production of camomile extracts. This consists of dried flowering heads including the attached stalk remains. The flowering heads consist of flower bases with enveloping calyx, 12 to 20 tongue-(ray-)florets and numerous tubular florets. The proportion of tongue florets in the whole drug is about 5 to 6%, the proportion of tubular florets 67 to 69%, and the rest is made up of flower bases with enveloping calyx and flower stalk.

Depending on the state of maturity of the flowering heads during harvesting, the nature of drying, processing, packaging, and storing of the drug, part of the whole drug disintegrates into its components parts, whereby camomile fragments, which consist essentially of tubular florets, and wing petals which consist mainly of tongue florets, are produced. These wing petals and camomile fragments are generally separated off during the recovery of the drug.

The camomile fragments and the wing petals are used in admixture with camomile fine-cut (that is, chopped camomile foliage) as a filling for tea bags. Camomile fragments are also used for the recovery of seed.

For the production of camomile extracts, the camomile whole drug, substantially freed from the fragments and wing petals, is normally used. However, the important flavone apigenin and the glycosides thereof are no longer present or are present only in small quantities in such a whole drug since these components mainly occur in the wing petals. Owing to the distinct musculotropic spasmolytic effect of apigenin and the equally spasmolytically effective apigenin glycosides, extracts with a high conent of these flavones are of therapeutic interest.

Since these wing petals have a substantially smaller content of volatile oil than the tubular florets or the intact flowering heads, they have so far not been used for the extraction of camomile with the purose of producing camomile extracts.

SUMMARY OF THE INVENTION

It has now surprisingly been found that, during extraction with the solvents normally used for the extraction of camomile, part of the flowering heads or the previously used whole drug can be replaced by wing petals without the content of volatile oil and of its components being reduced. A camomile extract with an increased flavone content (particularly apigenin and the glycosides thereof) is thereby obtained with a practically unchanged volatile oil content.

A camomile whole drug as described above (without fragments and wing petal constituents) or an ordinary camomile drug, without separation of the tubular florets and wing petals which have partially fallen off, is used for the process according to the invention. The camomile to be extracted (for example, camomile flowers, all varieties of the type *Matricaria recutita*) should, if possible, not be stored longer than a year under normal storage conditions since otherwise the loss of volatile oil and components thereof is too substantial. The camomile should be dried in the usual manner, for example, by forced air supply or also by drying in sunlight (at a temperature of, for example, from 30° to 70° C., optionally also up to 100° C.). Drying preferably takes place immediately after harvesting and in thin layers (for example, from 5 to 20 cm thick) at an air temperature of not greater than 50° C. and avoiding direct sunlight. The moisture content of the camomile drug to be used is generally from 3 to 15%, particularly from 8 to 10%.

A camomile drug (extraction material) with a volatile oil content of at least 750 mg %, for example, from 750 to 1200 mg %, an azulene content of at least 50 mg %, for example, from 50 to 250 mg %, and a bisabolol content of at least 150 mg %, for example, from 150 to 300 mg % is particularly suitable for the process according to the invention. The camomile can be a diploid or tetraploid camomile. A camomile drug according to German Pat. No. 24 02 802 (hereby incorporated by reference and relied upon), as well as German patent applications P No. 34 23 207 and P No. 34 46 216 is particularly suitable for the process according to the invention.

The wing petals used can be derived from the same camomile from which the drug is produced. Naturally, the wing petals can, however, also be derived from another camomile source.

The camomile wing petals used can be fresh or dried. By fresh camomile wing petals are to be understood those which are extracted within 24 hours of picking or which are frozen within this time.

The proportion of wing petals, which is added to the camomile drug is, for example, from 5 to 30, preferably from 10 to 20 parts by weight of the dried wing petals based on 100 parts by weight of the drug material used (a drug with a normal wing petal content of from 5 to 6% by weight of a drug from which the wing petals (tongue florets) have been removed by seiving).

The ratio of dried wing petals added to the dried camomile flowering heads (tubular florets and flower bases with enveloping calyx and a proportion of flower stalk) is for example: from 1 to 9 to from 1 to 2.3, preferably from 1 to 4 parts by weight. Should the wing petals be used in the form of fresh wing petals, a correspondingly higher amount by weight of wing petals is to be used (that is, the amount by weight which corresponds to the equivalent amount of drug). Generally, the amount of fresh wing petals used from 3 to 5 times, particularly from 4 to 5 time, the amount by weight which is used in the case of dried wing petals.

The wing petals (tongue florets) contain only about 12% of the volatile oil contained in the camomile flowers.

The camomile flowers and the wing petals can be used in a crushed state. In the case of flowers, it is, however, more flavorable if these are as uncrushed as possible. The wing petals can be homogeneously mixed with the camomile drug before extraction. Should the extraction take place using mixers, the wing petals are homogeneously mixed with the drug which is used during extraction; prior mixing of the wing petals and the drug is then unnecessary. Also, it is possible to extract the camomile flowers and the wing petals separately with the mentioned solvents and to join the extracts subsequently. In this connection, it might be advantageous to thicken the wing petal extract by careful treatment before joining with the flower extract.

For carrying out the process according to the invention, mixing apparatus, for example, so-called cavity mixers, percolators, and other suitable extraction apparatus can be used. The temperature during extraction is, for example, from 10° to 50° C. Cooling is not necessary.

Should the extraction take place by means of mixers, the rotation rate of the mixer should be adjusted, in particular so that in each case the rotational speed of a point on the periphery of the mixer is from 2.8 to 1.4 m/sec., the extraction time preferably being from 15 minutes to 3 hours, particularly from 30 to 120 minutes.

For a mixing device with a radius of 55 cm, a rotational speed of from 50 to 250 RPM is, for example, favorable, the extraction then being, for example, from 15 minutes to 3 hours. A rotational speed of from 50 to 250 RPM is preferably selected with a mixer of this size, in which case extraction time of from 15 to 120 minutes is sufficient.

Straight or branched aliphatic, mono-, or polyhydric alcohols having from 1 to 6 carbon atoms can be used as solvents, for example, methanol, ethanol, propan-2-ol, butanol, hexanol, glycerol, solketal (2-dimethyl-4-hydroxymethyl-1,3-dioxolan) and the like, as well as mixtures of these solvents with water.

Mixtures of these solvents can also be used. The minimum quantity of solvent is 2 parts of solvent to 1 part of drug. From 2 to 20 parts of solvent to 1 part of drug are generally used, particularly from 3 to 10 parts of solvent to 1 part of drug.

The camomile extracts obtained according to the invention contain at least 80, preferably from 90 to 170 mg % of natural flavones, in this case essentially apigenin and apigenin glucoside (calculated as apigenin).

The volatile oil content of the camomile extracts according to the invention is at least 80, preferably from 120 to 150 mg %.

The content of natural flavones (apigenin and the glucosides thereof) in the camomile extracts according to the invention, is at least 0.4, preferably from 0.425 to 0.8% by weight, based on the quantity of drug used with a wing petal proportion of from 5 to 30% by weight.

The azulene content in the extracts according to the invention is, for example, 3 mg %, preferably from 3 to 15 mg %.

The composition can comprise, consist essentially of, or consist of the stated materials; and the process can comprise, consist essentially of, or consist of the steps recited.

DETAILED DESCRIPTION

Example 1

A mixture of 320 g of camomile flowers (volatile oil 750 mg %; azulene 42 mg %) and 80 g of wing petals (volatile oil 196 mg %; azulene 0.4 mg %) is extracted with 2100 g of ethanol (40% by weight) in a cavity mixer with a rotational speed of the mixer of 65 RPM. After 90 minutes, the drug product is separated off by pressing, and the extract is filtered. The active ingredient content of the extract is determined in known manner:

| | |
|---|---|
| azulene | 10.4 mg % |
| volatile oil | 98.6 mg % |
| apigenin and apigenin glucosides (calculated as apigenin) | 141.0 mg % |
| extractive materials | 6.85% |

Comparative Example (Known Process)

400 g of camomile flowers (as given above) are extracted with 2100 g of ethanol (40% by weight) in a cavity mixer with a rotational speed of the mixer of 65 RPM. After 90 minutes, the drug product is separated off by pressing and the extract is filtered. The active ingredient content of the extract is determined in known manner:

| | |
|---|---|
| azulene | 11.2 mg % |
| volatile oil | 101.3 mg % |
| apigenin and apigenin glucosides (calculated as apigenin) | 65.3 mg % |
| extractive materials | 6.53% |

Example 2

A mixture of 240 g of camomile flowers (volatile oil 750 mg %; azulene 42 mg %), and 60 g of wing petals (volatile oil 196 mg %; azulene 0.4 mg %) is extracted with 2100 g of propan-2-ol (33% by weight) in a cavity mixer at 65 RPM. After 90 minutes, the drug product is separated off by pressing and the extract is filtered. The active ingredient content of the extract is determined in known manner:

| | |
|---|---|
| azulene | 4.9 mg % |
| volatile oil | 87.6 mg % |
| apigenin and apigenin glucosides (calculated as apigenin) | 106.4 mg % |
| extractive materials | 7.09% |

Comparative Example (Known Process)

300 g of camomile flowers (as given above) are extracted with 2100 g of propan-2-ol (33% by weight) in a cavity mixer at 65 RPM. After 90 minutes, the drug product is separated off by pressing and the extract is filtered. The active ingredient content of the extract is determined in known manner:

| | |
|---|---|
| azulene | 6.7 mg % |
| volatile oil | 82.1 mg % |
| apigenin and apigenin glucosides (calculated as apigenin) | 53.0 mg % |
| extractive materials | 6.6% |

What is claimed is:

1. A process of improving the efficiency of extracting camomile and producing a camomile extract rich in flavones comprising extracting a mixture of dried camomile flowering heads and additional camomile wing petals wherein the weight of added camomile wing petals on a dry basis to the camomile flowering heads is 1:9 to 1:2.3 parts by weight with a solvent which is an aliphatic alcohol or solketal or a mixture of such a solvent and water, said extract containing at least 80 mg% of volatile oil.

2. A process according to claim 1 wherein the solvent is a mixture of ethanol or propan-2-ol with water.

3. A process according to claim 1 wherein the extraction is continued until the extract contains between 80 and 150 mg% of volatile oil and between 80 and 170 mg% of natural flavone.

4. A process according to claim 1, wherein said extraction is conducted in a mixer-type extraction apparatus.

* * * * *